(12) United States Patent
Smith et al.

(10) Patent No.: US 8,316,692 B2
(45) Date of Patent: Nov. 27, 2012

(54) PARTICLE MONITOR AND METHOD USING AN ANALYSIS CHAMBER AND HEATED PURGE GAS

(75) Inventors: Kenneth Graham Smith, Wayville (AU); Mark Triggs, Willunga (AU)

(73) Assignee: Scantech International Pty Ltd., Camden Park (AU)

( * ) Notice: Subject to any disclaimer, the term of this patent is extended or adjusted under 35 U.S.C. 154(b) by 769 days.

(21) Appl. No.: 12/297,865

(22) PCT Filed: Apr. 19, 2007

(86) PCT No.: PCT/AU2007/000509
§ 371 (c)(1),
(2), (4) Date: Aug. 7, 2009

(87) PCT Pub. No.: WO2007/121511
PCT Pub. Date: Nov. 1, 2007

(65) Prior Publication Data
US 2010/0011843 A1 Jan. 21, 2010

(30) Foreign Application Priority Data
Apr. 20, 2006 (AU) .............................. 2006902074

(51) Int. Cl.
*G01N 1/20* (2006.01)
(52) U.S. Cl. .................... 73/28.01; 73/28.04; 73/863.41; 73/863.51; 73/863.81
(58) Field of Classification Search ............ 73/23.2, 73/23.3–23.34, 28.01–28.06, 31.01–31.03, 73/863, 863.21–863.41, 863.51, 863.81, 73/864, 864.33
See application file for complete search history.

(56) References Cited

U.S. PATENT DOCUMENTS

| | | | | | |
|---|---|---|---|---|---|
| 2,926,527 | A | * | 3/1960 | Crandall ..................... | 73/863.58 |
| 3,973,440 | A | * | 8/1976 | Vande Ven et al. ......... | 73/863.81 |
| 3,976,450 | A | * | 8/1976 | Marcote et al. .................... | 96/12 |
| 4,322,964 | A | * | 4/1982 | Melgaard et al. .............. | 73/1.06 |
| 4,557,419 | A | * | 12/1985 | Hall, II ........................ | 236/93 R |
| 4,890,479 | A | * | 1/1990 | Glover et al. ................. | 73/23.31 |
| 4,909,090 | A | * | 3/1990 | McGown et al. .......... | 73/864.33 |
| 4,914,297 | A | * | 4/1990 | Wieboldt et al. ............. | 250/343 |
| 5,109,201 | A | * | 4/1992 | Trerice et al. ................. | 324/642 |
| 5,173,662 | A | * | 12/1992 | Trerice et al. ................. | 324/642 |
| 5,222,389 | A | * | 6/1993 | Wong .......................... | 73/31.02 |
| 5,729,470 | A | * | 3/1998 | Baier et al. ...................... | 702/24 |
| 5,760,314 | A | * | 6/1998 | Bromberg et al. .......... | 73/863.21 |
| 6,151,953 | A | * | 11/2000 | Patashnick et al. .......... | 73/28.01 |

(Continued)

FOREIGN PATENT DOCUMENTS
EP 0475062 B2 3/1992
(Continued)

*Primary Examiner* — David Rogers
(74) *Attorney, Agent, or Firm* — Hamre, Schumann, Mueller & Larson, P.C.

(57) ABSTRACT

A particle monitor (1) including a module (3) for measuring a particle content of a sample, the module including an analysis chamber (4) for receipt of the sample and a heating unit (24) for maintaining an operating temperature of the chamber (4) and for heating the air used for purging the sample from the chamber (4). The invention also relates to a particle monitor (1) with a vibrator assembly (6) and to a particle monitor (1) with a valve assembly (8) for effecting a fast purge mode, for clearing a sample tube (5), and a slow purge mode.

20 Claims, 3 Drawing Sheets

U.S. PATENT DOCUMENTS

| | | | |
|---|---|---|---|
| 6,422,060 B1 * | 7/2002 | Patashnick et al. | 73/28.01 |
| 7,073,403 B2 * | 7/2006 | Albro et al. | 73/863.83 |
| 7,841,244 B2 * | 11/2010 | Barket et al. | 73/862.21 |
| 2003/0029221 A1 * | 2/2003 | Juneau et al. | 73/1.02 |
| 2003/0049854 A1 | 3/2003 | Rhodes | |
| 2003/0079524 A1 * | 5/2003 | Dahlin et al. | 73/28.02 |
| 2004/0107782 A1 * | 6/2004 | Bradley et al. | 73/864.34 |
| 2008/0148871 A1 * | 6/2008 | Himes et al. | 73/863.81 |
| 2008/0202261 A1 * | 8/2008 | Felix et al. | 73/863.23 |

FOREIGN PATENT DOCUMENTS

| | | |
|---|---|---|
| JP | 2002-210315 A | 7/2002 |
| SU | 844934 A | 7/1981 |
| SU | 940023 B * | 7/1982 |
| SU | 1594408 A1 | 9/1990 |
| WO | WO 02/09853 A1 | 2/2002 |

* cited by examiner ated in English as WO 2007/121511 on Nov. 1, 2007, which claims priority to Australian Patent Application No. 2006902074 filed Apr. 20 2006.

PARTICLE MONITOR AND METHOD USING AN ANALYSIS CHAMBER AND HEATED PURGE GAS

This application is U.S. National Phase of International Application PCT/AU2007/000509, filed Apr. 19, 2007 designating the U.S., and published in English as WO 2007/121511 on Nov. 1, 2007, which claims priority to Australian Patent Application No. 2006902074 filed Apr. 20 2006.

FIELD OF THE INVENTION

The present invention relates to a particle monitor particularly, but not exclusively, for monitoring carbon in fly ash.

BACKGROUND OF THE INVENTION

A fly-ash monitor measures the percentage carbon (% C) in samples of fly ash. The fly ash is produced by combustion of pulverised coal in a coal-burning power station. The fly-ash samples are automatically collected from a duct. Most power stations have several ducts of this type such that several monitors will normally be required.

A known form of monitor receives the fly ash in a sample tube housed within a detector chamber which utilises microwave radiation in a resonance cavity to determine the % C. The chamber is heated at an elevated operating temperature to prevent moisture content of the ash causing coagulation of the ash within the tube. A mesh filter is provided at a base of the tube to provide a seat, upon which the ash is collected. After testing, the ash is purged from the tube by a charge of air which is jetted through the mesh filter. Such a monitor has proven unreliable at times, presumably as a result of any of a number of possible causes such as contaminating material falling back into the tube after purging, ash blocking the filter to prevent complete purging and/or the air temperature of the purged air dropping below the operating temperature such that the ash sticks inside the sample tube.

OBJECT OF THE INVENTION

It is the object of the present invention to provide an improved monitor.

SUMMARY OF THE INVENTION

In accordance with the invention, there is provided a particle monitor including a module for measuring a particle content of a sample, the module including an analysis chamber for receipt of the sample and a heating unit for maintaining an operating temperature of the chamber and for heating the air used for purging the sample from the chamber.

Preferably, the heating unit heats the air and the chamber by heat transfer through a common heating block. More preferably, the heating block includes a tortuous flow path through which the air passes.

Preferably, the heating block weighs in the order of 5 kilograms and is heated to an operating temperature in the order of 130° C. The flow path is preferably designed to provide a surface area for heating the air in the order of 0.2 m².

In another aspect, there is provided a particle monitor having a sample tube for receipt of a sample to be analysed within an analysis chamber wherein a valve assembly is provided for switching between a fast purge mode for clearing the sample tube and a slow purge mode for maintaining the sample tube in a cleared condition.

Preferably, the monitor includes a pinch valve for providing a seat for the sample to accumulate within the sample tube. Preferably, the pinch valve is synchronised with the valve assembly, in order to open during the fast purge mode.

Preferably, the pinch valve includes a silicon rubber tubing and a pneumatic cylinder arranged to close the pinch valve with a spring bias.

In another aspect, there is provided a particle monitor including a sample tube for receipt of the sample and a vibrator assembly coupled at either end of a sample tube for compacting a sample within the sample tube.

BRIEF DESCRIPTION OF THE DRAWINGS

The invention is described, by way of non-limiting example only, with reference to the accompanying drawings, in which.

DETAILED DESCRIPTION OF THE DRAWINGS

Figure 1:
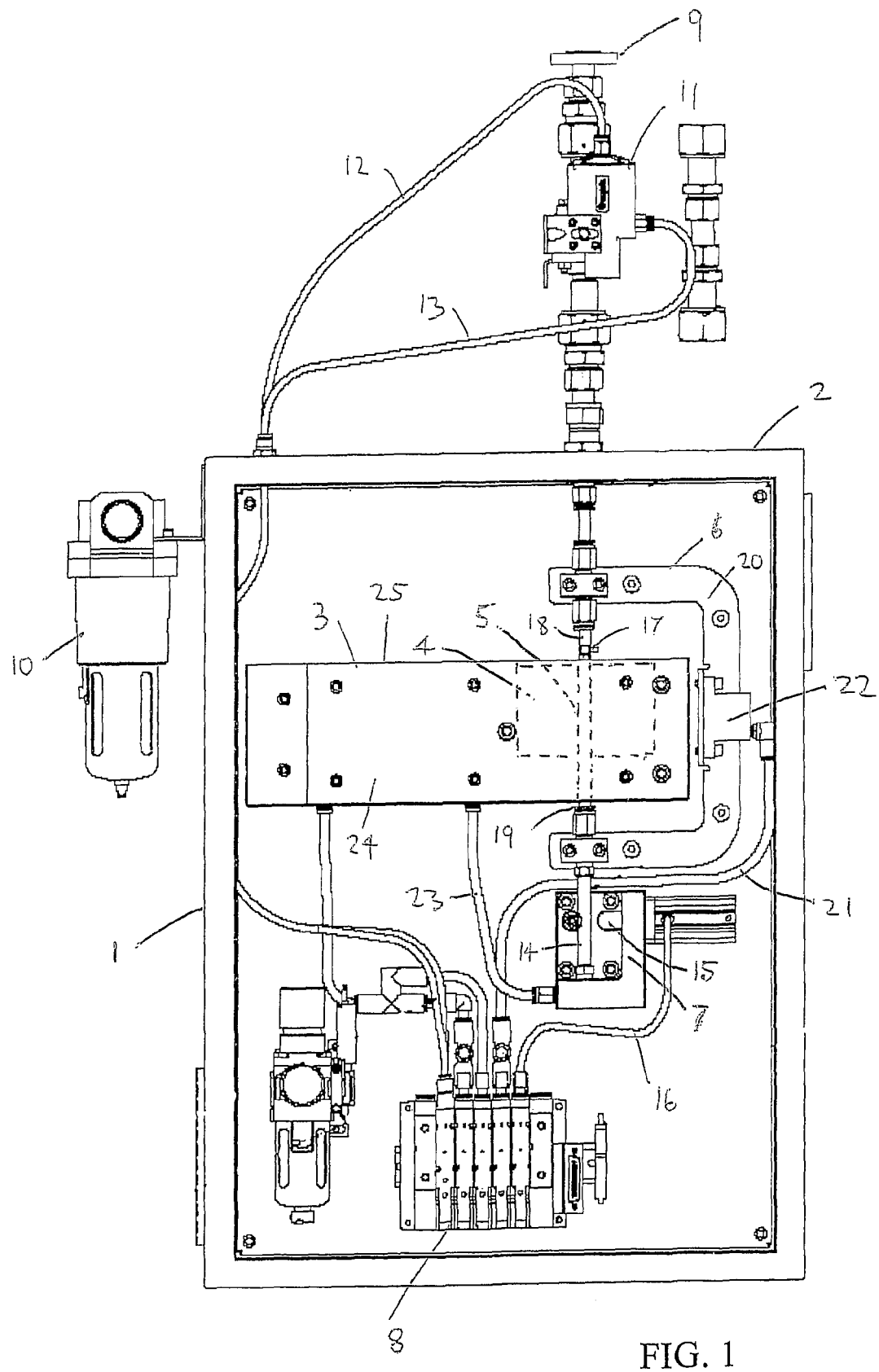
FIG. 1 is a front view of a particle monitor.
Figure 2:
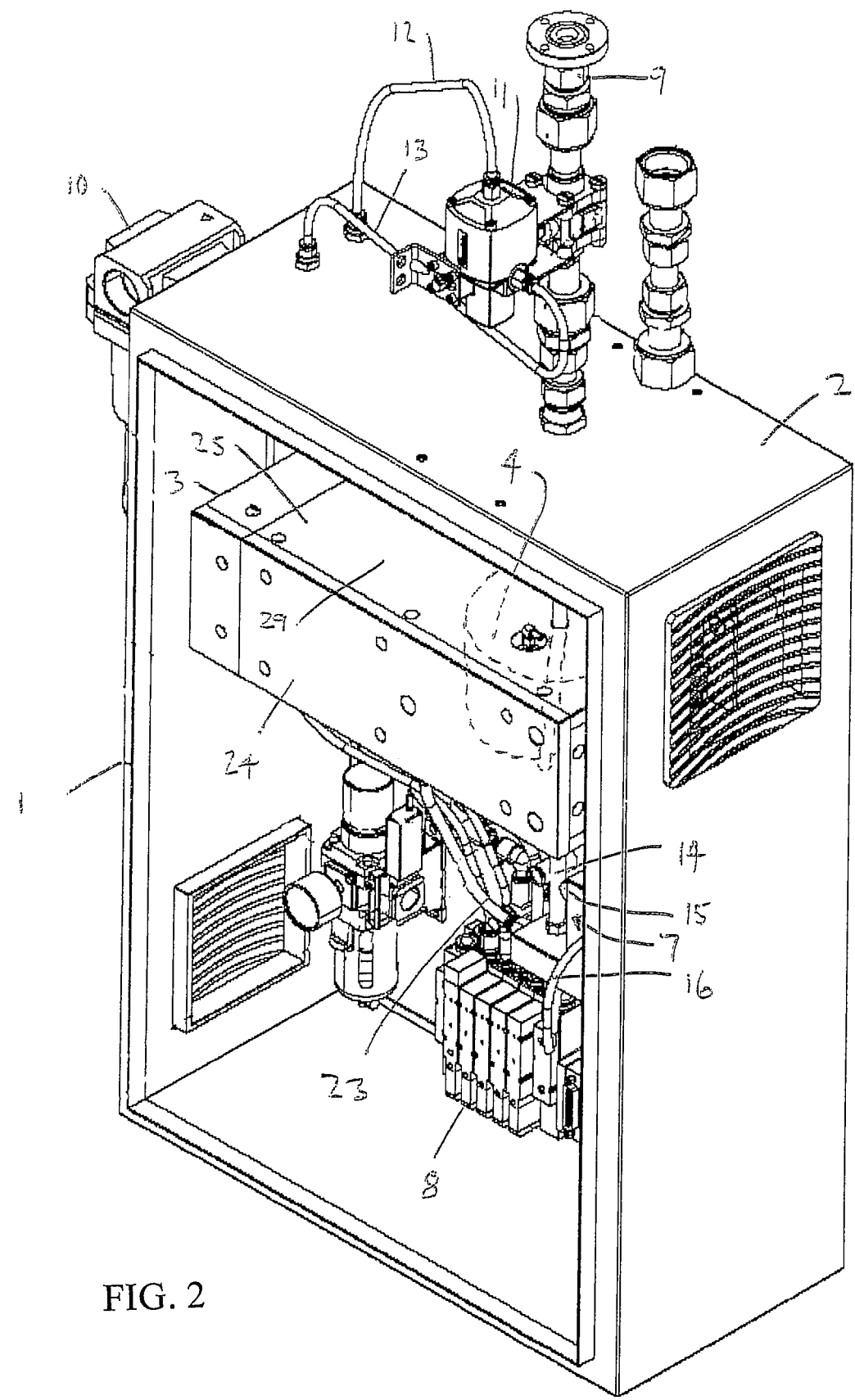
FIG. 2 is a perspective view of the particle monitor.
Figure 3:
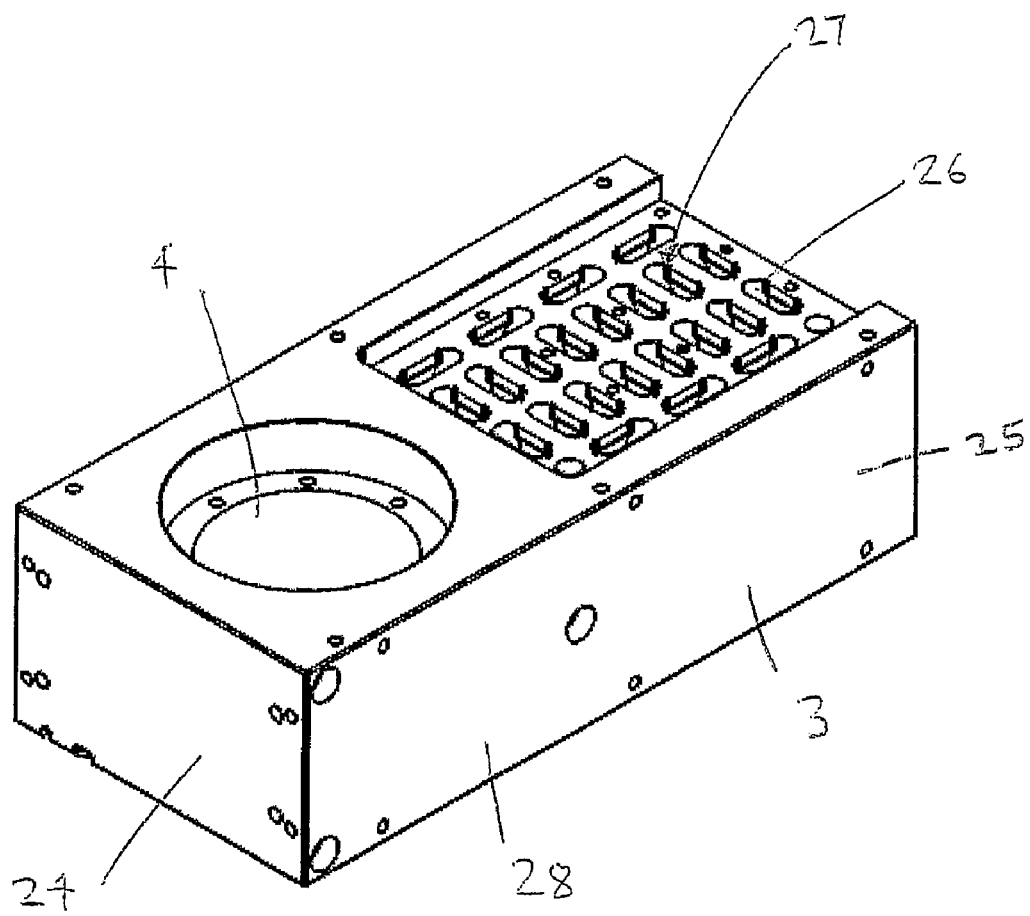
FIG. 3 is a perspective view of a base of an analysis module of the monitor of FIGS. 1 and 2.

A particle monitor 1 is shown in FIGS. 1 and 2 as having a cabinet housing 2 which contains an analysis module 3 that houses an analysis chamber 4 which receives a sample tube 5. The monitor 1 also includes a vibrator assembly 6 connected to the tube 5 above a pinch valve 7 and valve assembly 8 for controlling pneumatic fluid flow through the monitor 1.

A connector 9 is mounted to the cabinet housing 2 for coupling the monitor 1 to a fly-ash source such as a duct of a power station or the like (not shown). The connector 9 allows fly ash to be extracted from the duct for sampling and returned thereto during purging. A cyclone (not shown) for fly ash collection is typically attached to connector 9. A canister 10 is also mounted to the housing 2 for receipt of a purged sample for storage, if required, via interconnecting tubing (not shown).

In order to extract the fly ash from the duct, the valve assembly 8 is operated to establish air flow through conduits 12, 13 to move ball valve 11 to the collect position. The fly ash then drops down through the connector 9 and into the sample tube 5.

In order to capture the sample within the sample tube 5, the pinch valve 7 is actuated. The pinch valve includes a thick-walled silicon rubber sleeve 14 which is preferably rated to 230° C., in order to withstand the normal operating temperatures of the monitor, which are typically in the order of 130° C. The pinch valve 7 also includes a pneumatic cylinder 15 which is normally spring-biased into a closed position but which can be forced by pneumatic pressure along a connected pressure line 16, against the spring bias, in order to open the valve 7. When the valve 7 is closed, a seat is established upon which the fly ash can accumulate.

A suitable optical detector 17, or the like, may be provided at the top of the sample tube 5, in order to determine when sufficient fly ash is present within the tube, at which time analysis may be made. To ensure the sample is sufficiently compacted, the ends 18, 19 of the sample tube 5 may be agitated by the vibrator assembly 6, which is provided in the form of a generally U-shaped bracket 20, attached at either end 18, 19 of the tube 5. The bracket 20 is also connected to the valve assembly 8 via a pneumatic line 21 which couples into an air turbine vibrator 22, which serves to impart the appropriate mechanical agitation to the sample.

After vibrating the tube 5, the sample is then analysed by suitable resonant cavity analysis technique, within the analysis chamber 4 in a known manner.

Once analysis is complete, the valve assembly 8 is operated in order to switch into a fast purge mode where pressurised hot air from the analysis module 3 is injected through line 23 and into the sleeve 14. At the same time, the pinch valve 7 is opened, in order to effect a fast purge mode for clearing the sample tube 5 and ejecting the fly ash from the monitor 1 back into the connector 9, for either return to the duct or storage in the canister 10. After the purge operation is complete, the valve assembly 8 is then switched to a slow purge mode where the pressure delivered to line 23 is reduced to a level sufficient to maintain a clear condition of the sample tube 5 and prevent any unwanted fly ash falling back into the monitor 1.

The charge of pressurised heated air is preferably provided for a 20 second duration at a temperature of about 130° C. and a flow rate in the order of 6 to 12 liters per second. For that purpose, the analysis module 3 is also provided with a heating unit 24 which serves to heat not only the chamber 4 but also a substantial quantity of air that needs to be preheated for purging. In addition, the heating capacity of the unit 24 needs to be sufficient to maintain the continued slow purge mode. It has been found that forming the unit of a 5 kilogram heating block 25 of aluminium is suitable for satisfying such heating requirements but in order to provide sufficient surface area for heat exchange with the air, a flow path through the block 25 needs to be made substantially tortuous. Accordingly, the internal flow path 26 is formed by a number of drill holes 27 within a base 28 of the block 25 with joining channels at each end to create a multi-dimensional flow path through the block 25. The block 25 thereby forms a single unit 24 which can reliably satisfy heating needs of the air flow required for purging of the sample tube 5 whilst maintaining the analysis chamber 4 at a desired operating temperature.

Use of the pinch valve 7, in combination with the fast and slow purge modes also allows for reliable removal of ash from the sample tube after analysis, as compared to the prior art. In addition, the monitor 1 provides operational simplicity in that air flow required for extracting fly ash from a duct, compacting the fly ash, operating the pinch valve and purging the sample tube is all controlled by a single valve assembly 8.

The monitor 1 has been described with reference to its application in measuring the % C in samples of fly ash, however, it should be appreciated the particle monitor may also have application to any other field in which sample monitoring and analysis is required.

The invention claimed is:

1. A particle monitor for analyzing particles, comprising:
 an analysis chamber configured to receive a sample of particles for analysis therein;
 an analyzer configured to analyze the sample of particles in the analysis chamber;
 a purging system configured to introduce a pressurized purging gas into the analysis chamber to purge the sample from the analysis chamber; and
 a heating unit configured to maintain an operating temperature of the analysis chamber and pre-heat the purging gas used for purging the sample from the analysis chamber;
 wherein the heating unit pre-heats the purging gas and the analysis chamber by heat transfer through a common heating block; and
 wherein the heating block includes a tortuous flow path through which the purging gas passes to enhance heat transfer from the heating block to the purging gas.

2. A particle monitor as claimed in claim 1, wherein the heating block weighs in the order of 5 kilograms and is heated to an operating temperature in the order of 130° C.

3. A particle monitor as claimed in claim 1, wherein the heating unit provides a surface area for pre-heating the purging gas in the order of 0.2 m$^2$.

4. A particle monitor as claimed in claim 1, wherein the particles are fly ash particles and the analyzer measures a content of unburned carbon in the fly ash particles.

5. A particle monitor as claimed in claim 1, wherein the particles are fly ash particles and the analyzer measures a content of unburned carbon in the fly ash particles.

6. A particle monitor as claimed in claim 1, wherein the particles are fly ash particles and the analyzer measures a content of unburned carbon in the fly ash particles.

7. A particle monitor as claimed in claim 1, wherein the purging gas is compressed air.

8. A particle monitor as claimed in claim 1, wherein the heating unit pre-heats the purging gas by heat transfer from a heating block.

9. A particle monitor as claimed in claim 8, wherein the particles are fly ash particles and the analyzer measures a content of unburned carbon in the fly ash particles.

10. A particle monitor for analyzing particles, comprising:
 an analysis chamber configured to receive a sample of particles for analysis therein;
 an analyzer configured to analyze the sample of particles in the analysis chamber;
 a purging system configured to introduce a pressurized purging gas into the analysis chamber to purge the sample from the analysis chamber; and
 a heating unit configured to maintain an operating temperature of the analysis chamber and to pre-heat the purging gas used for purging the sample from the analysis chamber;
 wherein the heating unit pre-heats the purging gas and the analysis chamber by heat transfer through a common heating block;
 wherein the heating block includes a tortuous flow path through which the purging gas passes to enhance heat transfer from the heating block to the purging gas, and
 further comprising a valve assembly configured to switch from a fast purge mode for clearing the analysis chamber to a slow mode for maintaining the analysis chamber in a cleared condition.

11. A particle monitor as claimed in claim 10, further comprising a pinch valve for provides a seat for the sample of particles to accumulate within the analysis chamber.

12. A particle monitor as claimed in claim 11, wherein the pinch valve is synchronized with the valve assembly, in order to open during the fast purge mode.

13. A particle monitor as claimed in claim 12, wherein the pinch valve comprises a silicon rubber tubing and a pneumatic cylinder configured to close the pinch valve with a spring bias.

14. A particle monitor for analyzing particles, comprising:
 an analysis chamber configured to receive a sample of particles for analysis therein;
 an analyzer configured to analyze the sample of particles in the analysis chamber;
 a purging system configured to introduce a pressurized purging gas into the analysis chamber to purge the sample from the analysis chamber; and
 a heating unit configured to maintain an operating temperature of the analysis chamber and to pre-heat the purging gas used for purging the sample from the analysis chamber;

wherein the heating unit pre-heat the purging gas and the analysis chamber by heat transfer through a common heating block;

wherein the heating block includes a tortuous flow path through which the purging gas passes to enhance heat transfer from the heating block to the purging gas, and further comprising a vibrator assembly coupled to the analysis chamber to compact the sample of particles within the analysis chamber.

15. A particle monitoring method, comprising:
receiving a sample of particles into an analysis chamber for analysis therein;
analyzing the sample of particles in the analysis chamber;
purging the sample from the analysis chamber using a pressurized gas;
maintaining an operating temperature of the analysis chamber; and
pre-heating the gas used for purging the sample from the analysis chamber;
wherein said pre-heating includes passing the purging gas through a tortuous flow path in a heating block to enhance heat transfer from the heating block to the purging gas.

16. A particle monitoring method as claimed in claim 15, wherein the particles are fly ash particles and the analyzing measures a content of unburned carbon in the fly ash particles.

17. A particle monitoring method, comprising:
receiving a sample of particles into an analysis chamber for analysis therein;
analyzing the sample of particles in the analysis chamber;
purging the sample from the analysis chamber using a pressurized gas;
maintaining an operating temperature of the analysis chamber; and
re-heating the gas used for purging the sample from the analysis chamber;
wherein said purging includes switching from a fast purge mode for clearing the analysis chamber to a slow purge mode for maintaining the analysis chamber in a cleared condition.

18. A particle monitoring method as claimed in claim 17, wherein the particles are fly ash particles and the analyzing measures a content of unburned carbon in the fly ash particles.

19. A particle monitoring method as claimed in claim 17, wherein compressed air in used in the purging.

20. A particle monitoring method, comprising:
receiving a sample of particles into an analysis chamber for analysis therein;
analyzing the sample of particles in the analysis chamber;
purging the sample from the analysis chamber using a pressurized gas;
maintaining an operating temperature of the analysis chamber;
pre-heating the gas used for purging the sample from the analysis chamber; and
vibrating the analysis chamber to compact the sample of particles therein.

* * * * *